United States Patent
Le Corre

(10) Patent No.: US 7,894,879 B2
(45) Date of Patent: Feb. 22, 2011

(54) DEVICE ENABLING AN INDIVIDUAL TO SELF-MONITOR HIS BREATHING IN ORDER TO ASSIST IN THE CONTROL OF A RADIOTHERAPY OR IMAGING UNIT

(76) Inventor: Patrick Le Corre, 12 Rue Clement Ader, Muret (FR) 31600

( * ) Notice: Subject to any disclaimer, the term of this patent is extended or adjusted under 35 U.S.C. 154(b) by 1359 days.

(21) Appl. No.: 11/396,591

(22) Filed: Apr. 4, 2006

(65) Prior Publication Data
US 2006/0219244 A1  Oct. 5, 2006

Related U.S. Application Data

(60) Provisional application No. 60/670,282, filed on Apr. 12, 2005.

(30) Foreign Application Priority Data

Apr. 4, 2005  (FR)  .................................. 05 03282

(51) Int. Cl.
*A61B 5/05* (2006.01)
(52) U.S. Cl. ...................... 600/427; 600/411; 600/529
(58) Field of Classification Search .............. 600/529, 600/533, 534, 538, 410, 411, 413, 418, 427, 600/428
See application file for complete search history.

(56) References Cited

U.S. PATENT DOCUMENTS

| | | | | |
|---|---|---|---|---|
| 5,067,494 A | * | 11/1991 | Rienmueller et al. | 600/428 |
| 5,949,080 A | | 9/1999 | Ueda et al. | |
| 6,597,939 B1 | | 7/2003 | Lampotang et al. | |
| 6,633,775 B1 | | 10/2003 | Bernard | |
| 7,050,537 B2 | * | 5/2006 | Tsujii | 378/95 |
| 2006/0129044 A1 | * | 6/2006 | Le Corre | 600/428 |

FOREIGN PATENT DOCUMENTS

| | | |
|---|---|---|
| FR | 2 823 679 | 10/2002 |
| WO | WO 99/43260 | 9/1999 |
| WO | WO02085455 | * 10/2002 |

\* cited by examiner

*Primary Examiner*—Charles A Marmor, II
*Assistant Examiner*—Michael D'Angelo
(74) *Attorney, Agent, or Firm*—Young & Thompson

(57) ABSTRACT

A device enabling an individual to self-monitor his breathing in order to assist in the control of a radiotherapy or imaging unit includes elements for acquiring a current metabolic volume signal, a signal-processing unit and a communication interface. The device also includes elements capable of detecting regular breathing during rest and then of forcing the communication interface to communicate a signal representing a predetermined setpoint value.

12 Claims, 2 Drawing Sheets

DEVICE ENABLING AN INDIVIDUAL TO SELF-MONITOR HIS BREATHING IN ORDER TO ASSIST IN THE CONTROL OF A RADIOTHERAPY OR IMAGING UNIT

BACKGROUND OF THE INVENTION

The invention relates to a device enabling an individual to self-monitor his breathing in order to assist in the control of a radiotherapy unit for the treatment of tumours or an imaging unit.

The tumours are ones located in the region of the thoracic cage (lungs, breast, etc.) or tumours, the position of which varies as a function of expansion of the thorax (liver, etc.)

One of the major difficulties in radiotherapy is that of irradiating the tumour with rays, especially X-rays, while limiting as far as possible irradiation of healthy tissues located in the immediate vicinity of the tumour. Also, in the treatment of a tumour, the patient is conventionally invited to inflate his lungs as far as possible in order to achieve a state in which there is a minimum amount of tissue per unit of surface area and also to achieve optimally uniform ray penetration of the infected tissues to be treated. Once the practitioner has judged the inflation to be satisfactory, the patient is invited to hold his breath and to maintain an apnea during the irradiation process.

Lung ventilation capacity, which results in the capacity to inflate or to contract the lungs, varies from person to person. Moreover, different individuals experience stress differently, so some people have difficulty in controlling their breathing and therefore in stabilising the organ to be treated.

Furthermore, various devices have been developed, on the one hand, for helping the practitioner to control a radiotherapy unit and, on the other hand, for helping the patient to achieve adequate levels of inflation or contraction of the lungs for the treatment that he has to undergo.

FR-2.823.679, for example, describes a device for controlling a radiotherapy unit comprising means for measuring the expansion of the thorax of a patient and a control unit capable of comparing, in a first stage, the measured values of the expansion of the thorax with stored values of the expansion of the patient's thorax during rest and for triggering, in a second stage, the irradiation process once the measured values reach pre-established thorax expansion limit values and correspond to an inflation of the lungs capable of qualitative treatment. This device is also provided with display means allowing the patient and the practitioner to visualise the development over time of the expansion of the thorax and the triggering values to be reached before radiotherapy may be undergone.

Although the characteristics of this device are established, especially owing to its widespread use in hospital centres, it does not allow the most stressed patients to reach the desired triggering levels. Indeed, it has been found that a stressed patient who sees from a display device that his level of lung expansion is far from the limit to be reached will tend to force his breathing. This will, at best, enable him to reach this triggering level of lung expansion, but will not allow him to hold his breath for a sufficiently long time and in a sufficiently stable manner—a necessary condition for safe irradiation.

The device described in WO 99/43260 is a device helping to trigger the irradiation process by analysing a specific number of parameters that reflect the state of a patient's breathing—air flow rate, pressure, estimated lung volume, and $CO_2$ concentration—and are fed to the input of a control unit capable of triggering, under the supervision of the practitioner, the irradiation process once the compiling of these parameters reveals nominal lung expansion conditions for the patient in question.

This device helps the practitioner to choose the right moment for triggering the irradiation process, but does not allow the patient either to visualise or to monitor the moment of irradiation.

SUMMARY OF THE INVENTION

The invention aims to overcome the aforementioned drawbacks and to help to calm down an individual forced to undergo a course of radiotherapy by proposing a device enabling the patient to self-monitor his breathing.

Another objective of the invention is to provide a device that enables an individual to self-monitor his breathing and allows him to follow and monitor the development over time of his breathing cycles.

Another objective of the invention is to provide a device for facilitating improved observations by an imaging unit, by improving and by monitoring an individual's ability to hold his breath.

Another objective of the invention is to provide a device that is responsive to variations in an individual's breathing cycles, so the individual is gradually able to reach a predetermined state.

The invention accordingly relates to a device enabling an individual to self-monitor his breathing in order to assist in the control of a radiotherapy or imaging unit comprising:
  means for acquiring at least one signal, known as the current metabolic volume signal, which is representative of the variation in the volume of air contained in the lungs of an individual during his breathing cycles,
  a signal-processing unit connected to said acquisition means, said processing unit comprising means for accessing at least one value, known as the rest value, which is representative for an individual of a breathing cycle during rest, and at least one value, known as the setpoint value, which is representative for an individual of a predetermined target inhalation and/or exhalation,
  at least one interface for communication with an individual, said communication interface being connected to said processing unit and comprising communication means capable of communicating a signal to the individual.

The self-monitoring device according to the invention is characterised in that the unit for processing the signals:
  comprises means for detecting regular breathing during rest by comparing the current metabolic volume signal with said rest value(s)
  and is capable of controlling said communication means in order that said means transmit a signal that is representative of said setpoint value(s) if said signal-processing unit detects regular breathing during rest.

A device according to the invention allows, on the one hand, regular breathing during rest, beneficial for initiating predetermined inhalation or exhalation, to be detected and, on the other hand, the predetermined target inhalation or exhalation level to be communicated to an individual. A device according to the invention also allows the process of preparing an individual prior to a radiotherapy session to be broken down into two stages: a first stage corresponding to a phase in which the individual breathes freely, at his own rate, thus enabling the individual to achieve a state of calmness; and a second stage, which guides the individual toward predetermined target inhalation and/or exhalation. This support is provided by the communication of a signal, which, on the one hand, informs the individual that nominal breathing conditions have been achieved and, on the other hand, renders the breathing levels to be achieved compatible with radiotherapy. This two-stage preparation process helps the individual to relax by self-managing his breathing. The patient himself is entrusted with the process of preparation for the subsequent radiotherapy session.

Moreover, a device according to the invention, when associated with an imaging unit, also helps said imaging unit to obtain qualitative negatives owing to the quality of the inhalations and/or exhalations performed by an individual using the device.

Advantageously and according to the invention, the signal-processing unit comprises:
- means for detecting non-regular breathing and means for detecting inhalation and/or exhalation reaching the setpoint value(s), by comparing the current metabolic volume signal with said rest value(s) and with said setpoint values(s) respectively,
- and is capable of controlling said communication means in order that said means do not transmit a signal that is representative of said setpoint value(s) if said processing unit detects non-regular breathing and if no inhalation and/or exhalation reaching the setpoint value(s) is/are detected.

A device according to the invention is thus provided with means adapted in such a way that regular breathing during rest causes the transmission of a signal representing at least one setpoint value and that unsettled, non-regular breathing cuts off the transmission of said signal, thus preventing any attempted target inhalation and/or exhalation and promoting a rapid return to a state of calmness.

Advantageously and according to the invention, regular breathing during rest is defined by at least three successive breathing cycles during rest, and non-regular breathing is defined by less than three breathing cycles during rest.

It has been found that the three breathing cycles during rest ensure that the individual is in the regular breathing phase during rest. In a variation, regular breathing during rest is defined by at least five regular breathing cycles during rest.

Advantageously and according to the invention, the processing unit is capable of controlling the communication means in order that said means continuously transmit a signal correlated with said current metabolic volume signal.

In a variation, the signal is also communicated to an external operator to allow him to monitor the progress of the signal over time.

Advantageously and according to the invention, the means for acquiring said metabolic volume signal comprise a spirometer.

The spirometer is the best means for measuring variation in the volume of air contained in an individual's lungs during his breathing cycles. Moreover, a spirometer allows a correlation to be established between an expansion of the thorax, i.e. a given exhalation and/or inhalation, and the corresponding volume of air. On the other hand, a spirometer advantageously allows a precise correlation to be established between the volume of air contained in an individual's lungs and the position of the organ to be treated. This type of instrument therefore allows the position of the organ to be treated to be reproduced in a substantially identical manner from one session to the next.

Advantageously and according to the invention, the rest and setpoint values, which are representative of a breathing cycle during rest and of a predetermined target inhalation and/or exhalation, are the rest ventilation level at the end of the breathing cycle during rest and the volume of air contained in an individual's lungs, corresponding to the predetermined target inhalation and/or exhalation, respectively.

Advantageously and according to the invention, the communication means comprise display means capable of displaying, as a signal correlated with the current metabolic volume signal, a curve, which is representative of the variation in the volume of air contained in the lungs of an individual during his breathing, and of displaying, as a signal representing said setpoint value(s), one or more bars positioned at the setpoint value(s) superimposed on said curve, thus enabling an individual to visualise the predetermined target inhalation and/or the predetermined target exhalation.

A visual signal displayed in the form of a curve, to which a bar, positioned at the setpoint value, is added, is an item of data that may easily be interpreted by an individual and effectively informs the individual of the state of his breathing and the setpoint value.

In a variation or in combination, the communication means comprise sound communication means capable of transmitting, as a signal correlated with said current metabolic volume signal, a signal, the frequency of which is correlated with the current metabolic volume signal, and of transmitting, as a signal representing the setpoint value(s), another signal of predetermined frequency.

This variation provides an effective means for adapting a device according to the invention to enable a partially-sighted person to self-monitor-his breathing.

Advantageously and according to the invention, the display means comprise glasses provided with at least one liquid crystal display and capable of being worn by the individual.

These glasses allow an individual to monitor the changing variation in the current metabolic volume signal and also the target inhalation and/or exhalation levels that may be achieved, if these levels are displayed.

In a variation or in combination, the display means comprise screens arranged in the immediate vicinity of the individual, allowing the individual to visualise the signals transmitted by the communication means.

Advantageously and according to the invention, the means for accessing the rest and setpoint values comprise storage means.

Advantageously and according to the invention, these storage means comprise at least one external memory device.

Advantageously and according to the invention, these storage means also comprise a range of rest and setpoint values that is representative of a margin of measurement relative to the measurements of the expansion of the thorax during rest and of a margin of measurement relative to the target inhalation and/or exhalation measurements, respectively.

The measurement ranges are advantageously calculated in such a way that the tolerance relative to the nominal rest value and the nominal inhalation or exhalation value is approximately 0.1 litres. The purpose of this tolerance is to allow for possible variations from one breathing cycle to another.

These rest and setpoint value ranges are parameterable.

A device according to the invention is advantageously connected to a control unit, which is capable of controlling the irradiation of an individual by a radiotherapy unit if the communication means of the communication interface have communicated said signal representing the setpoint value(s) and if the measurements of the expansion of the individual's thorax correspond to the predetermined setpoint value(s).

A device according to the invention is also advantageously used with an imaging unit so as to determine the setpoint values that are compatible with a qualitative irradiation process for the relevant tumour. In practice, the device according to the invention will, in a first prior training phase, be coupled to an imaging unit and, in a second phase, be connected to a control unit capable of controlling a radiotherapy unit.

The invention extends to a method carried out by and in a device according to the invention. The invention thus extends to a method enabling an individual to self-monitor his breathing in order to assist in the control of a radiotherapy or imaging unit, which method includes the following steps:

acquiring at least one signal, known as the current metabolic volume signal, which is representative of the variation in the volume of air contained in an individual's lungs during his breathing cycles, accessing at least one value, known as the rest value, which is representative for an individual of a breathing cycle during rest, and at least one value, known as the setpoint value, which is representative for an individual of a predetermined target inhalation and/or exhalation.

The method according to the invention is characterised in that it includes the following steps:

detecting regular breathing during rest by comparing the current metabolic volume with said rest value(s), and communicating to the individual a signal representing said setpoint value(s) if regular breathing during rest is detected.

Advantageously and according to the invention, the method also includes the following steps:

detecting non-regular breathing by comparing the current metabolic volume signal with said rest values, detecting predetermined target inhalation and/or exhalation, by comparing the current metabolic volume signal with said setpoint value(s), and ceasing to communicate said signal representing said setpoint value(s) if non-regular breathing is detected and if no target inhalation and/or exhalation has/have been detected.

Advantageously and according to the invention, regular breathing during rest is defined by at least three successive breathing cycles during rest, and non-regular breathing is defined by less than three successive breathing cycles during rest.

Advantageously and according to the invention, the method includes the step of continuously communicating to the individual a signal correlated with said current metabolic volume signal.

Advantageously and according to the invention, the step of acquiring the current metabolic volume signal is carried out using a spirometer.

Advantageously and according to the invention, the step of communicating to the individual a signal correlated with the current metabolic volume signal consists in displaying a curve representing the variation in the volume of air contained in an individual's lungs during his breathing.

Advantageously and according to the invention, the step of communicating a signal representing said setpoint value(s) consists in displaying, superimposed on the curve representing the variation in the volume of air contained in an individual's lungs during his breathing, one or more bars positioned at said setpoint value(s), thus enabling the individual to visualise said predetermined target inhalation and/or exhalation.

Advantageously and according to the invention, the step of communicating to the individual a signal correlated with the current metabolic volume signal is carried out using glasses provided with at least one liquid crystal display and capable of being worn by an individual.

In a variation and according to the invention, the step of communicating to the individual a signal correlated with the current metabolic volume signal also includes a step consisting in transmitting a sound signal, the frequency of which is correlated with said current metabolic volume signal.

Advantageously and according to this variation, the step of communicating a signal representing said setpoint value(s) consists in transmitting a signal of predetermined frequency.

Advantageously and according to the invention, the step of accessing said rest and setpoint values consists in accessing storage means.

The invention also relates to a device capable of carrying out a method according to the invention.

The invention further relates to a device enabling an individual to self-monitor his breathing, characterised in combination by all or some of the foregoing or following characteristics.

Other characteristics, objects and advantages of the invention will become clear on reading the following description, which presents an embodiment of the invention by way of non-limiting example and with reference to the accompanying drawings, in which:

DESCRIPTION OF PREFERRED EMBODIMENTS

Figure 1:
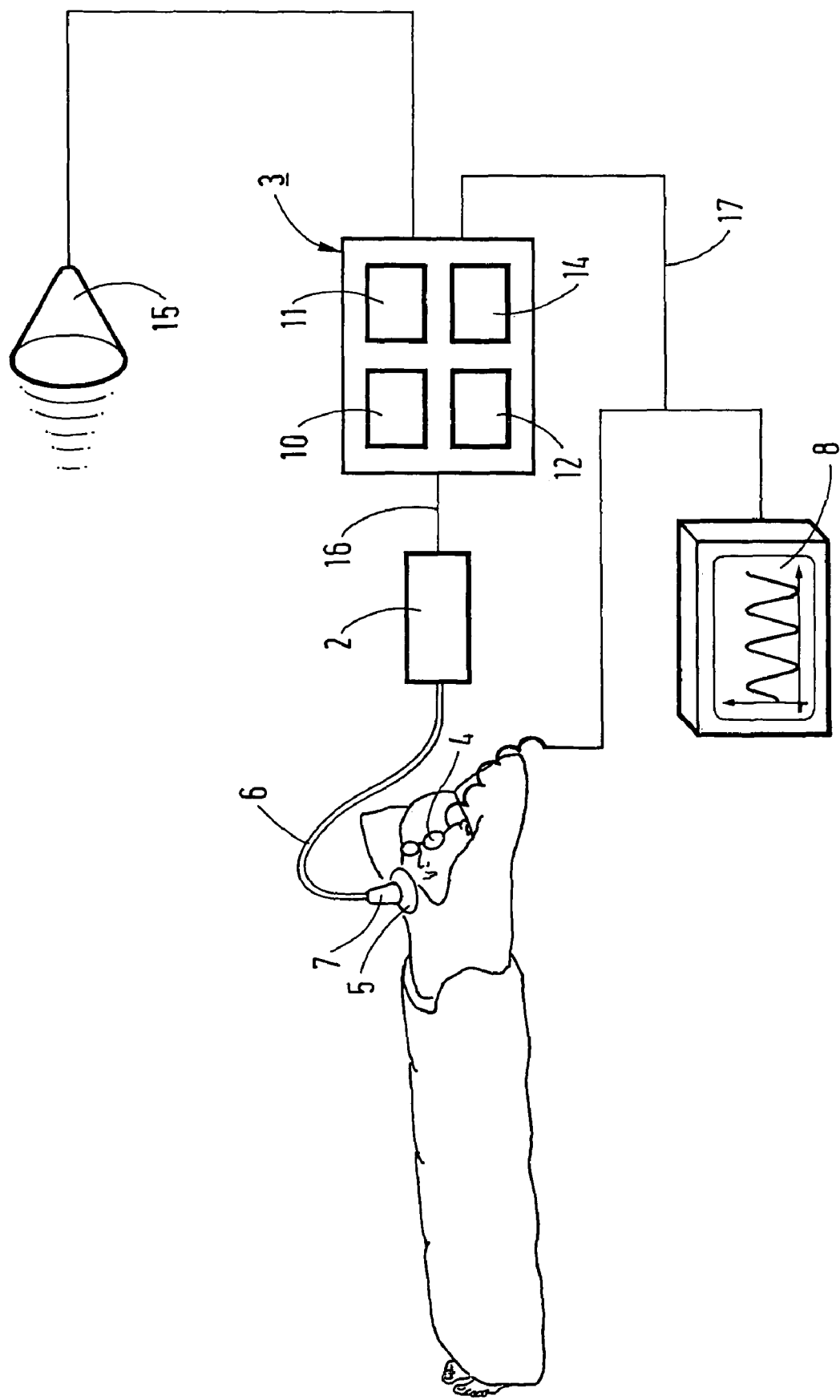
FIG. 1 is a block diagram of a device enabling an individual to monitor his breathing in order to assist in the control of a radiotherapy unit.

The control-assisting device illustrated in FIG. 1 comprises a pneumotachograph-type spirometer 2 comprising a sensor integrating differences in pressure in the flow of breathing and capable of delivering an electric signal representing the volume of air corresponding to the expansion of the thorax.

According to the embodiment of FIG. 1, the spirometer 2 is connected to a mouthpiece 5 by a pliable hose 6, at the end of which an interchangeable bacterial filter 7 is inserted. The spirometer 2 also includes means for heating the integrating sensor to a stabilised temperature, such as an electrical resistor, which means are permanently powered so as to eliminate the moisture produced by the individual's breathing, which is liable to bring about the opposing case of significant errors in the volume calculations.

The spirometer 2 used is, according to the embodiment of FIG. 1, a spirometer as described in FR-2.823.679.

The spirometer 2 is connected, according to an embodiment of the present invention, to a signal-processing unit 3 via a USB-type connection 16. The processing unit 3 consists, according to the embodiment of FIG. 1, of a central microcomputer unit, but may, according to other embodiments, comprise a DSP or any other computer and/or processor-type system capable of processing digital or analogue data.

The processing unit 3 also comprises means for accessing rest and setpoint values, respectively. The term "means for accessing values" refers conventionally to means and channels for obtaining these values. Accessing a value is therefore the process for retrieving and the means for obtaining this value from a memory, or from any storage element, which covers disks, tapes or any external medium as well as the cache memories and RAMs of the central units.

According to the embodiment of FIG. 1, the access means consist of storage means 14, which are preferably mass storage means such as a microcomputer hard disk. According to other embodiments, these storage means 14 comprise at least one exchangeable recording medium such as a floppy disk, a magneto-optical disk, an optical disk, an electronic memory key, particularly of the USB type, an electronic memory card, etc.

The processing unit 3 also comprises means 10 for detecting regular breathing during rest. These detecting means are, according to an embodiment of the present invention, digital means capable of sampling the signal acquired by the spirometer, comparing each sample with the rest value, storing the result of the comparison and transmitting a signal for the detection of regular breathing during rest if the stored results of the comparison display at least three consecutive matches.

According to another embodiment, these detecting means 10 means may be analogue detecting means or combined analogue and digital means.

The processing unit 3 is connected to a communication interface, which, according to the embodiment of FIG. 1, comprises a display device consisting of a microcomputer screen 8 and a pair of glasses 4 comprising two liquid crystal displays. On controlling the signal-processing unit 3, this graphic communication interface allows, on the one hand, a curve 13 representing an individual's breathing cycles to be displayed and, on the other hand, if the detecting means have detected regular breathing during rest, a bar 9 positioned at each of the setpoint values additionally to be displayed. According to another embodiment, the liquid crystal glasses are replaced by small screens arranged in the vicinity of the individual.

Data is exchanged between the signal-processing unit 3 and the display device via series wire connections 17, for example of the USB type.

A device according to the invention for monitoring an individual's breathing is used as described above.

The preparation stage basically consists, according to an embodiment of the invention, in determining and storing at least one value, known as the rest value, which is representative of a breathing cycle during rest, and at least one value, known as the setpoint value, which is representative of a target inhalation and/or exhalation level. This target level is determined by a practitioner and corresponds to a level subsequently allowing qualitative radiotherapy to take place.

Other additional stages are required prior to radiotherapy, but these stages are beyond the scope of this invention, which relates solely to the device enabling an individual to self-monitor his breathing.

The first value is determined while the individual is breathing normally during rest, by measuring his current metabolic volume and storing a rest value Vr which represents the individual's rest ventilation level at the end of the cycle during rest.

The second value, on the other hand, is determined while the individual inhales or exhales deeply, by noting the inhalation and/or exhalation level at which the tumour is in its optimal position for subsequent radiotherapy treatment. The stored value, known as the setpoint value Va, therefore corresponds to the inhalation and/or exhalation level at which the irradiation process will then be triggered when the individual holds his breath at this level for subsequent radiotherapy treatment. In order to help this value to be determined, the device according to the invention is beneficially coupled to a scanner-type imaging unit, so the practitioner may visualise the position of the tumour and determine which level of inhalation or exhalation leads to optimal positioning of the organ subsequently to be treated.

According to an embodiment, the measured values are values with a margin of 0.1 litres. The ranges of values [Vr−0.1, Vr+0.1] and [Va−0.1, Va+0.1] are thus known as the stability zone 18 and the setpoint zone 19, respectively. The margins of measurement are parameterable and may be adapted to the individual using the device. These margins of measurement may not be symmetrical relative to the nominal value.

These values are, according to the embodiment of FIG. 1, stored in a microcomputer memory 14 or, according to other embodiments of the present invention, stored on exchangeable media.

Figure 2:
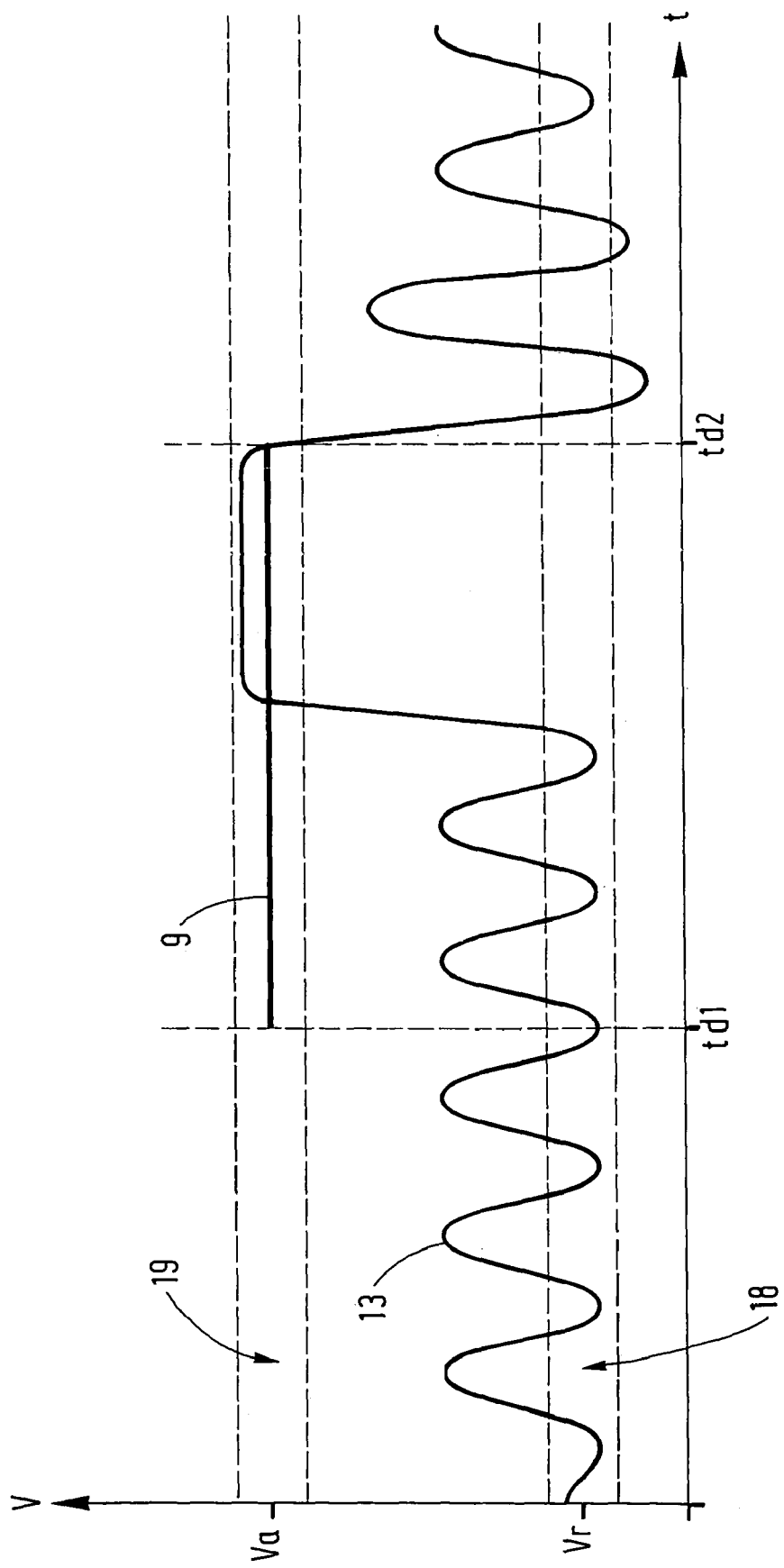
FIG. 2 is a graph showing a breathing curve of an individual, as presented to this individual according to an embodiment of the present invention.

FIG. 2 shows a curve 13 representing the volume of air in an individual's lungs during his breathing cycles. The y-axis denotes volume, and the x-axis time. Vr denotes the ventilation level during rest, which is used as a reference for detecting a breathing cycle during rest, and Va denotes the volume of air corresponding to a target inhalation. The stability zone 18 and the setpoint zone 19 are denoted by broken lines. The reference td1 denotes the moment from which the signal-processing unit 3 detects that the individual has achieved regular breathing during rest, defined by at least three breathing cycles during rest. From this moment, a bar 9 positioned at the setpoint value, in other words at the volume Va, is superimposed on the curve. The reference td2 denotes the moment from which the signal-processing unit 3 has detected that the individual is no longer holding his breath and non-regular breathing during rest has set in, thus causing the bar 9, positioned at the value Va, to disappear.

The displaying and the disappearance of the bar 9 depend on detections carried out by the detecting means of the signal-processing unit 3. According to an embodiment of the present invention, these detecting means 10, 11, 12 are based on the following structure: the detecting means 10, 11, 12 isolate, in a first stage, the breathing cycles (by detecting two local maximums separated by a local minimum, or two local minimums separated by a local maximum) and determine, in a second stage, for each isolated breathing cycle, if the low level of the cycle is located in the stability zone 18. If three successive cycles have a ventilation level during rest pertaining to the stability zone, regular breathing is detected and the bar at the setpoint value is displayed on the display means 4, 8.

If the following cycle has a ventilation level during rest outside the stability zone, non-regular breathing is detected and the bar disappears. According to an embodiment of the present invention, three successive cycles, each having a ventilation level during rest within the stability zone, are then required for the bar 9, positioned at said setpoint value, to reappear. According to another embodiment, in the event of three breathing cycles during rest having been detected and the fourth being outside the stability zone, if the fifth is then within the stability zone, the bar 9 will reappear, breathing being considered to be regular during rest.

If the bar 9 is displayed and a new regular breathing cycle during rest is not detected, two scenarios may occur, in order of decreasing priority. In the first scenario, the detecting means 12 detect that the signal representing the variation in the volume of air contained in the individual's lungs has reached the setpoint zone 19; in this case, the bar 9 continues to be displayed until the signal leaves the setpoint zone. In the second scenario, the detecting means 11 detect non-regular breathing; in this case, the bar 9 disappears unless the first scenario also occurs, in which case, as mentioned above, the bar continues to be displayed.

According to the embodiment of FIG. 1, the graph of FIG. 2 is conveyed to the individual via liquid crystal glasses 4 or screens arranged in the vicinity of the individual, thus enabling the individual using the device according to the invention to monitor his breathing in real time and himself to determine the moment at which he starts the target inhalation or exhalation. In practice, this target inhalation or exhalation is timed such that the individual holds his breath, thus enabling the position of the tumour to be kept under conditions compatible with radiotherapy.

According to an embodiment of the present invention, the self-monitoring device is connected to a control unit capable of triggering, on the instructions of a specialised practitioner, the process for the irradiation of the individual once said individual has held his breath under the aforementioned conditions. According to this embodiment, the irradiation process is terminated once the individual ceases to hold his breath.

A self-monitoring device according to the invention therefore enables an individual rapidly to enter a favourable psychological state by effectively managing his sense of stress, thus ensuring the effectiveness of radiotherapy treatment.

The invention claimed is:

1. Self-monitoring device enabling an individual to self-monitor his breathing in order to assist in the control of a radiotherapy or imaging unit comprising:
    means for acquiring at least one current metabolic volume signal, which is representative of the variation in the volume of air contained in the lungs of an individual during his breathing cycles;
    a signal-processing unit connected to said means for acquiring, said processing unit comprising means for accessing at least one rest value, which is representative of a metabolic volume for an individual of a breathing cycle during rest, and at least one setpoint value, which is representative of a metabolic volume for an individual of a predetermined target inhalation and/or exhalation; and
    at least one interface for communication with an individual, said communication interface being connected to said signal-processing unit and comprising communication means capable of communicating a signal to the individual,
    wherein the signal-processing unit comprises means for detecting regular breathing during rest by comparing the current metabolic volume signal with said rest value(s) and is capable of controlling said communication means in order that said means transmit a signal that is representative of said setpoint value(s) if said signal-processing unit detects regular breathing during rest,
    wherein the signal-processing unit further comprises means for detecting non-regular breathing and means for detecting inhalation and/or exhalation reaching the setpoint value(s), by comparing the current metabolic volume signal with said rest value(s) and with said setpoint values(s) respectively,
    and is capable of controlling said communication means in order that said means do not transmit a signal that is representative of said setpoint value(s) if said processing unit detects non-regular breathing and if no inhalation and/or exhalation reaching the setpoint value(s) is/are detected.

2. Self-monitoring device according to claim 1, wherein said regular breathing during rest is defined by at least three successive breathing cycles during rest, and said non-regular breathing is defined by less than three breathing cycles during rest.

3. Self-monitoring device according to claim 1, wherein the signal-processing unit is capable of controlling said communication means in order that said means continuously transmit a signal correlated with said current metabolic volume signal.

4. Self-monitoring device according to claim 1, wherein the means for acquiring said current metabolic volume signal comprise a spirometer.

5. Self-monitoring device according to claim 1, wherein said rest and setpoint values are a ventilation level when an individual is at rest at the end of his breathing cycle during rest and a volume of air contained in the lungs of an individual corresponding to said predetermined target inhalation and/or said predetermined target exhalation, respectively.

6. Self-monitoring device according to claim 1, wherein the communication means comprise display means capable of displaying, as a signal correlated with the current metabolic volume signal, a curve, which is representative of the variation in the volume of air contained in the lungs of an individual during his breathing, and of displaying, as a signal representing said setpoint value(s), one or more bars positioned at said setpoint value(s) superimposed on said curve, thus enabling an individual to visualise said predetermined target inhalation and/or said predetermined target exhalation.

7. Self-monitoring device according to claim 6, wherein the display means comprise glasses provided with at least one liquid crystal display and capable of being worn by the individual.

8. Self-monitoring device according to claim 1, wherein the communication means comprise sound communication means capable of transmitting, as a signal correlated with said current metabolic volume signal, a signal, the frequency of which is correlated with said current metabolic volume signal, and of transmitting, as a signal representing said setpoint value(s), another signal of predetermined frequency.

9. Self-monitoring device according to claim 1, wherein the means for accessing said rest and setpoint values comprise storage means.

10. Self-monitoring device according to claim 9, wherein the storage means comprise at least one external memory device.

11. Self-monitoring device according to claim 9, wherein the storage means also comprise a range of rest and setpoint values that is representative of a margin of measurement relative to the measurements of the ventilation level during rest and of a margin of measurement relative to the target inhalation and/or exhalation measurements, respectively.

12. Assembly comprising the self-monitoring device according to claim 1 and a control unit capable of controlling the irradiation of an individual by a radiotherapy unit if said communication means of said communication interface of said self-monitoring device have communicated said signal representing said setpoint value(s) and if the measurements of the expansion of the individual's thorax correspond to said predetermined setpoint value(s).

* * * * *